(12) United States Patent
Coumans et al.

(10) Patent No.: US 10,814,009 B2
(45) Date of Patent: Oct. 27, 2020

(54) SELECTIVE REDUCTION OF CYSTEINE-ENGINEERED ANTIBODIES

(71) Applicant: Byondis B.V., Nijmegen (NL)

(72) Inventors: Rudy Gerardus Elisabeth Coumans, Nijmegen (NL); Henri Johannes Spijker, Nijmegen (NL)

(73) Assignee: Byondis B.V., Nijmegen (NL)

( * ) Notice: Subject to any disclaimer, the term of this patent is extended or adjusted under 35 U.S.C. 154(b) by 242 days.

(21) Appl. No.: 16/099,123

(22) PCT Filed: Feb. 13, 2017

(86) PCT No.: PCT/EP2017/053157
§ 371 (c)(1),
(2) Date: Nov. 5, 2018

(87) PCT Pub. No.: WO2017/137628
PCT Pub. Date: Aug. 17, 2017

(65) Prior Publication Data
US 2019/0388552 A1   Dec. 26, 2019

(30) Foreign Application Priority Data

Feb. 12, 2016 (EP) ..................................... 16155481
Dec. 23, 2016 (EP) ..................................... 16206761

(51) Int. Cl.
*A61K 47/68* (2017.01)
*C07K 16/30* (2006.01)
*A61K 45/06* (2006.01)

(52) U.S. Cl.
CPC ...... *A61K 47/6803* (2017.08); *A61K 47/6851* (2017.08); *C07K 16/30* (2013.01);
(Continued)

(58) Field of Classification Search
None
See application file for complete search history.

(56) References Cited

FOREIGN PATENT DOCUMENTS

| WO | WO2006/034488 | 3/2006 |
|----|---------------|--------|
| WO | WO2006/134174 | 12/2006 |

(Continued)

OTHER PUBLICATIONS

B.-Q. Shen et al., "Conjugation site modulates the in vivo stability and therapeutic activity of antibody-drug conjugates" Nature Biotechnology, Feb. 2012, 30 (2), 184-189.

(Continued)

*Primary Examiner* — Karl J Puttlitz
(74) *Attorney, Agent, or Firm* — Buscher Patent PLLC

(57) ABSTRACT

The present invention relates to a process for the selective reduction of cysteine-engineered antibodies comprising reacting an antibody comprising one or more engineered cysteines at positions selected from HC40, HC41, HC42, HC89, HC152, HC153, HC155, HC171, LC40, LC41, LC165, and LC168 with a compound according to formula (I), (II), (III), (IV), (V), (VI) or (VII): (I) (II) (III) (IV) (V) (VI) (VII), and to a process for the preparation of antibody conjugates, including antibody-drug conjugates (ADCs).

(I)

(Continued)

-continued

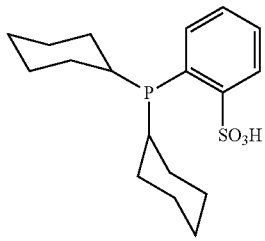
(II)

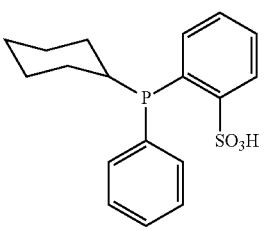

(III)

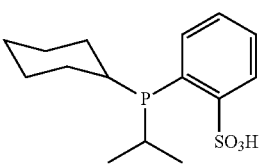

(IV)

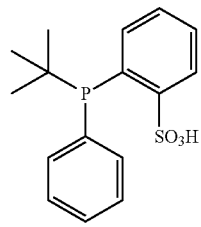

(V)

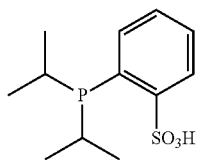

(VI)

-continued

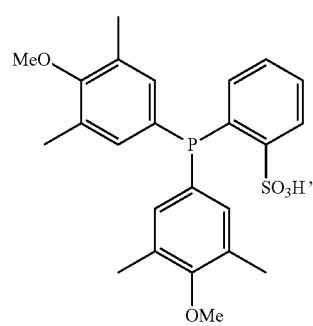
(VII)

20 Claims, 2 Drawing Sheets

(52) U.S. Cl.
CPC .......... *A61K 45/06* (2013.01); *C07K 2317/31* (2013.01); *C07K 2317/77* (2013.01)

(56) References Cited

FOREIGN PATENT DOCUMENTS

| WO | WO2011/133039 | 10/2011 |
|---|---|---|
| WO | WO2015/123265 | 8/2015 |
| WO | WO2015/177360 | 11/2015 |

OTHER PUBLICATIONS

C.R. Behrens et al., "Methods for site-specific drug conjugation to antibodies" MAbs, Jan.-Feb. 2014, 6(1), 46-53.
Kabat, E.A. et al., Sequences of Proteins of Immunological Interest, 5th Ed. Public Health Service, National Institutes of Health, Bethesda, MD., NIH publication No. 91-3242, pp. 662, 680, 689 (1991).
M. Bornand et al., "Mechanistically Design Dual-Site Catalysts for the Alternating ROMP of Norbornene and Cyclooctene" Organometallics, 2007, 26(14), 3585-3596.
T. Schultz et al., "Palladium(II) Complexes with Chelating P, O-Ligands as Catalysts for the Heck Reaction" Synthesis, Feb. 21, 2005, 6, 1005-1011.
Doronina et al., "Enhanced Activity of Monomethylauristatin F through Monoclonal Antibody Delivery: Effects of Linker Technology on Efficacy and Toxicity" Bioconjugate Chem., 2006, 17, 114-124.

SELECTIVE REDUCTION OF CYSTEINE-ENGINEERED ANTIBODIES

FIELD OF THE INVENTION

The present invention relates to a process for the selective reduction of cysteine-engineered antibodies and to a process for the preparation of antibody conjugates including antibody-drug conjugates (ADCs).

BACKGROUND OF THE INVENTION

Cysteine-engineered antibodies are increasingly used for conjugation of a therapeutic moiety (e.g. a drug or toxin), a radiopharmaceutical, a fluorescent label or a hydrophilic polymer. The introduction of a cysteine residue at a suitable position of the antibody allows control of the site of conjugation and the obtained site-specific conjugates are more homogeneous than the conjugates obtained via wild-type conjugation, i.e. conjugation via interchain disulfide cysteines. Such wild-type conjugation leads to a heterogeneous mixture of conjugates, which is especially disadvantageous in the case of ADCs. Some individual constituents of a wild-type conjugated ADC mixture can have poor in vivo performance. The in vivo performance of ADCs in terms of efficacy, safety, and stability may be improved if the linker drugs of the ADCs are site-specifically conjugated via engineered cysteines according to B.-Q. Shen et al., Nature Biotechnology, 2012, 30 (2), 184-189.

Methods for site-specific drug conjugation to antibodies are comprehensively reviewed by C. R. Behrens et al., MAbs, 2014, 6(1), 46-53. The first site-specific conjugation approach was developed at Genentech by introducing an engineered cysteine residue using site-directed mutagenesis at positions showing high thiol reactivity as elaborated in WO2006/034488. This common practice in protein modification is more complicated in an antibody because of the various native cysteine residues already present. Introducing the extra cysteine residue in an unsuitable position could result inter alia in improper formation of interchain disulfide bonds and therefore improper folding of the antibody.

WO2015/177360 of Synthon Biopharmaceuticals discloses advantages of conjugating linker drugs to engineered cysteine residues at specific positions in the Fab and Fc parts of monoclonal antibodies.

Engineered cysteine residues in suitable positions of the mutated antibody are usually capped by other thiols, such as cysteine or glutathione, to form disulfides. These capped residues need to be uncapped before drug attachment can occur. To achieve this, the following conventional reduction procedure is used: first, complete reduction of all interchain disulfide bonds and capped engineered cysteines with tris (2-carboxyethyl)phosphine hydrochloride (TCEP) or dithiothreitol (DTT) to obtain free cysteine residues, followed by mild oxidation, typically using dehydroascorbic acid (DHAA), to reform the antibody's interchain disulfide bonds. Under optimal conditions, two drugs per antibody (i.e. drug-to-antibody ratio, DAR, is 2) will be attached (if one cysteine is engineered into the heavy chain or light chain of the monoclonal antibody (mAb)). However, this conventional approach has several disadvantages. Complete reduction followed by mild re-oxidation of the wild-type interchain disulfide bonds may lead to incorrect reformation of these disulfide bonds, resulting in the formation of mAb half body (i.e. one heavy chain and one light chain instead of two of each), and "scrambled disulfides", i.e. disulfide bonds between cysteines that were not paired in the original unreduced antibody, generating additional free cysteine residues available for conjugation, resulting in a heterogeneous ADC mixture. Moreover, DHAA is instable in water, which complicates the mild re-oxidation process.

To tackle this issue, Seattle Genetics developed a selective reduction strategy using mild reducing agents, such as the amino acid cysteine. Those agents reduce capped engineered cysteines at a higher rate than the interchain disulfide bonds, as disclosed in WO2015/123265. However, free cysteine can auto-oxidize to cystine, free glutathione can oxidize to glutathione disulfide, and mixed disulfides can be formed. All these disulfides can recap the engineered cysteines, reversing the initial reduction. This problem was solved by continuously removing the formed cystine, e.g. by tangential flow filtration (TFF) using an ultra-filtration membrane. This solution, however, is disadvantageous as it requires a considerable modification of the standard equipment for drug conjugation. Moreover, a significant amount of reduction of the interchain disulfide bonds was observed, even under the most optimal reaction conditions.

Even for proteins that are not antibodies, few examples exist of processes for selective reduction of capped engineered cysteines. WO2006/134174 of Novo Nordisk discloses a process wherein triphenylphosphine-3,3',3"-trisulfonic acid (TPPTS) is used to selectively reduce a capped engineered cysteine in coagulation factor VIIa, followed by PEGylation of the protein. The native disulfide bonds are left intact only in the presence of a large excess of an active site inhibitor. However, the present inventors found that TPPTS reduces the interchain disulfide bonds of monoclonal antibodies, concluding that it is not a suitable agent for the selective reduction of engineered cysteines in monoclonal antibodies.

Therefore, there is a need for new methods for selectively reducing cysteine-engineered antibodies.

BRIEF DESCRIPTION OF THE INVENTION

The present invention provides a process for the selective reduction of a cysteine-engineered antibody. It further provides a process for the preparation of antibody conjugates, including antibody-drug conjugates (ADCs).

DETAILED DESCRIPTION OF THE INVENTION

Figure 1:
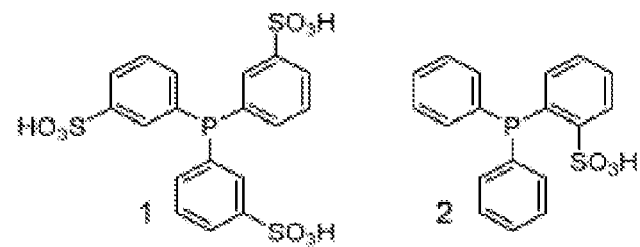
FIG. 1 shows an SDS-PAGE gel run under non-reducing conditions of reaction mixtures of a heavy chain 41 engineered cysteine (HC41C) anti-PSMA antibody incubated with four different reducing agents in lanes 1, 2, 3 and 4 for 8 days at ambient temperature. The numbering of the structures corresponds with the lanes.
Figure 1:
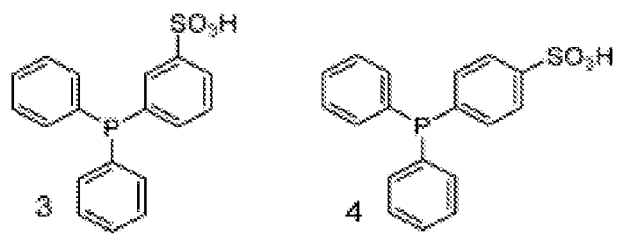
Figure 1:
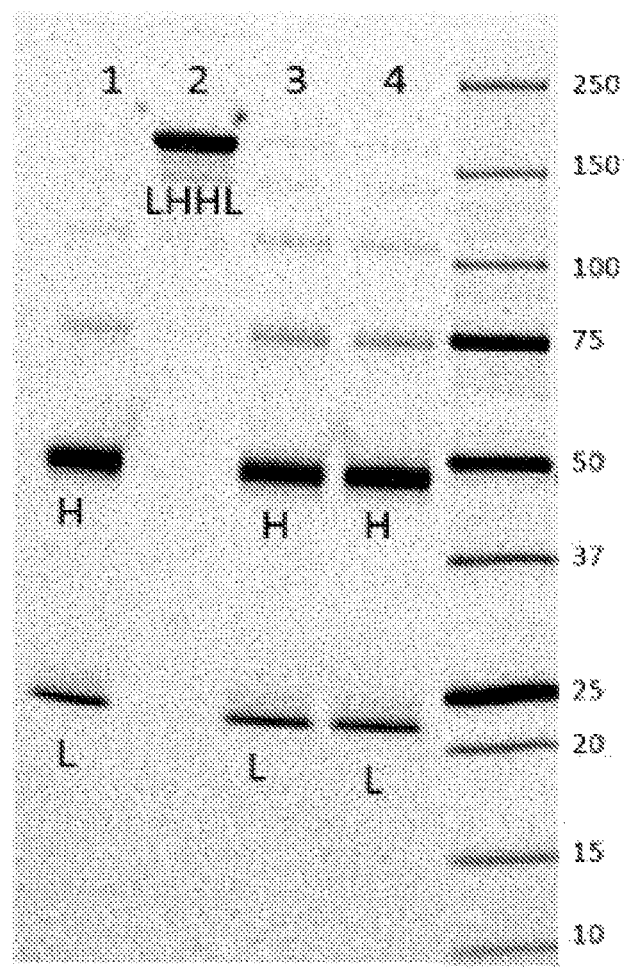

The present invention relates to a process for the selective reduction of a cysteine-engineered antibody comprising reacting an antibody comprising one or more engineered cysteines at positions selected from heavy chain 40, 41, 42 and 89 according to the Kabat numbering system, heavy chain 152, 153, 155, and 171 according to the Eu numbering system, light chain 40 and 41 according to the Kabat numbering system, and light chain 165 and 168 according to the Eu numbering system, with a compound according to formula (I), (II), (III), (IV), (V), (VI) or (VII):

(I)
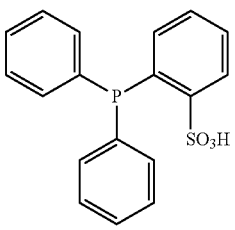

(II)
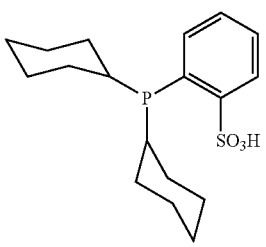

(III)
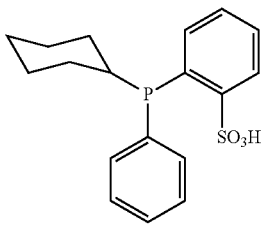

(IV)
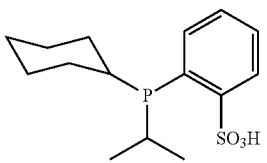

(V)
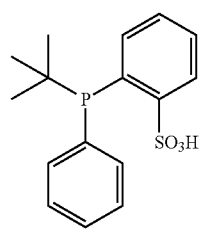

(VI)
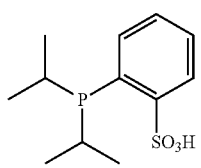

(VII)
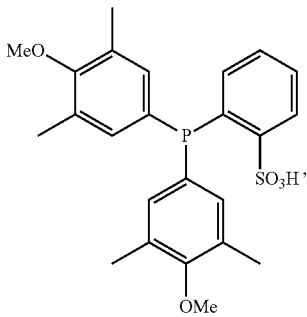

or a salt thereof

In the context of the present invention, Kabat numbering is used for indicating the amino acid positions of engineered cysteines in the heavy chain (HC) and light chain (LC) variable regions and Eu numbering is used for indicating the positions in the heavy chain and light chain constant regions of the antibody. The expression "Kabat numbering" refers to the numbering system used for heavy chain variable domains or light chain variable domains of the compilation of antibodies in Kabat, E. A. et al., Sequences of Proteins of Immunological Interest, 5th Ed. Public Health Service, National Institutes of Health, Bethesda, Md. (1991).

The expression "Eu numbering" refers to the Eu index as in Kabat, E. A. et al., Sequences of Proteins of Immunological Interest, 5th Ed. Public Health Service, National Institutes of Health, Bethesda, Md., NIH publication no. 91-3242, pp. 662, 680, 689 (1991).

In the description of the present invention the presence of an engineered cysteine, for example at heavy chain position 41 of an antibody may be abbreviated as HC41C, at light chain position 41 of an antibody may be abbreviated as LC41C, etc.

The compound according to formula (I), (II), (III), (IV), (V), (VI) or (VII) acts as a reducing agent in the process of the invention. The compound according to formula (I) is 2-(diphenylphosphino)benzenesulfonic acid and the compound according to formula (II) is 2-(dicyclohexylphosphino)benzenesulfonic acid. Phosphines (I) and (II) are commercially available as the sulfonic acid or as the sodium sulfonate salt from various suppliers, e.g. Sigma-Aldrich. The compound according to formula (III), (IV), (V), (VI) or (VII) may be prepared by known procedures in the art (analogous to procedures disclosed in e.g., M. Bornand et al., Organometallics, 2007, 26(14), 3585-3596 and T. Schultz et al., Synthesis, 2005, 6, 1005-1011). The compounds according to formulae (I), (II), (III), (IV), (V), (VI) and (VII) are readily deprotonated in aqueous solution and may form corresponding sulfonate salts with cations present in the solution. Typical cations are, e.g., ammonium, tetramethylammonium, triethanolammonium, imidazolium, sodium, and potassium, i.e. cations present in common buffer solutions.

Preferred in accordance with the present invention is a process wherein the cysteine-engineered antibody is reacted with a compound according to formula (I), (II), (V), (VI) or (VII) or a salt thereof Also preferred in accordance with the present invention is a process wherein the cysteine-engineered antibody is reacted with a compound according to formula (I), (II) or (III) or a salt thereof.

More preferred in accordance with the present invention is a process wherein the cysteine-engineered antibody is reacted with a compound according to formula (I) or (II) or a salt thereof.

Most preferred in accordance with the present invention is a process wherein the cysteine-engineered antibody is reacted with a compound according to formula (I) or a salt thereof.

The present inventors found inter alia that by using a reducing agent according to formula (I), (II), (III), (IV), (V), (VI) or (VII), the capped engineered cysteines at specific positions in the Fab cavity that is formed by the CH1, VH, VL and CL domains of the antibody are selectively reduced, while the interchain disulfide bonds formed by native cysteine residues are left intact. This completely eliminates the formation of mAb half body and of antibodies with scrambled disulfides.

Preferred is a process according to the present invention wherein the antibody comprises one or more engineered cysteines at positions selected from HC40, HC41, HC42, HC152, HC153, LC40, LC41, and LC165. More preferred is a process according to the present invention wherein the antibody comprises one or more engineered cysteines at positions selected from HC41, HC42, LC40, and LC41. Most preferred is a process according to the present invention wherein the antibody comprises one cysteine at position 41 on the heavy chain (i.e. HC41C).

Alternatively, the process according to the invention comprises reacting an antibody comprising one or more engineered cysteines at positions selected from heavy chain 40, 41, 89, 152, 153, 155, and light chain 40, 41, 165 and 168 with a compound as defined above. Preferred is a process according to the present invention wherein the antibody comprises one or more engineered cysteines at positions selected from HC40, HC41, HC152, HC153, LC40, LC41, and LC165. More preferred is a process according to the present invention wherein the antibody comprises one or more engineered cysteines at positions selected from HC41, LC40, and LC41.

In accordance with the present invention, the cysteine-engineered antibody may be prepared by using conventional molecular cloning techniques or the heavy chain or light chain domain(s) of the antibody carrying the cysteine mutation(s) can be synthesized as such using known (peptide or DNA) synthesis equipment and procedures. Typically, procedures similar to those disclosed in WO2015/177360 are used.

In accordance with the present invention, the term "antibody" means a full antibody or a fragment thereof wherein interchain disulfide bonds are present, e.g. a F(ab')$_2$ or a Fab fragment.

The antibody to be used in accordance with the present invention may be of any of the following isotypes: IgG, i.e. IgG$_1$, IgG$_2$, IgG$_3$ and IgG$_4$, IgM, IgA$_1$, IgA$_2$, secretory IgA (sIgA), IgD, and IgE. Preferably, the antibody is of the IgG isotype, more preferably the antibody is of the IgG$_1$ isotype or IgG$_2$ isotype. An IgG$_1$ antibody having κ light chains is most preferred. Preferably, the IgG antibody carries a native glycoside/carbohydrate moiety attached at N297 of the heavy chain of the antibody.

The antibody to be used in the process of the present invention may be a monospecific (i.e. specific for one antigen) antibody or a bispecific (i.e. specific for two different antigens) antibody. In one embodiment of the present invention, the antibody is a monospecific antibody (or a fragment thereof wherein interchain disulfide bonds are present).

These antibodies may be produced recombinantly, synthetically, or by other suitable methods known in the art.

Preferably, the antibody binds to an antigen target that is expressed in or on the cell membrane (e.g., on the cell surface) of a tumour cell. More preferably, the antibody is internalised by the cell after binding to the (antigen) target.

Typically, an antibody which could be used in the process of the present invention is a monospecific antibody against one of the targets selected from the group consisting of annexin A1, B7H4, CA6, CA9, CA15-3, CA19-9, CA125, CA242, CCR2, CCR5, CD2, CD19, CD20, CD22, CD30, CD33, CD37, CD38, CD40, CD44, CD47, CD56, CD70, CD74, CD79, CD115, CD123, CD138, CD203c, CD303, CD333, CEA, CEACAM, CLCA-1. CLL-1, c-MET, Cripto, CTLA4, DLL3, EGFL, EGFR, EPCAM, EPh antibodies, such as EphA2 or EPhB3, ETBR, FAP, FcRL5, FGF, FGFR3, FOLR1, GCC, GPNMB, HER2, HMW-MAA, integrin, IGF1R, L6, Lewis A like carbohydrate, Lewis X, Lewis Y, LIV1, mesothelin, MUC1, MUC16, NaPi2b, Nectin-4, PSMA, PTK7, SLC44A4, STEAP-1, 5T4 (or TPBG, trophoblast glycoprotein), TF (tissue factor), TF-Ag, Tag72, TNF, TROP2, VEGF and VLA.

Examples of suitable antibodies include blinatumomab (CD19), epratuzumab (CD22), iratumumab and brentuximab (CD30), vadastuximab (CD33), tetulumab (CD37), isatuximab (CD38), bivatuzumab (CD44), lorvotuzumab (CD56), vorsetuzumab (CD70), milatuzumab (CD74), polatuzumab (CD79), rovalpituzumab (DLL3), futuximab (EGFR), oportuzumab (EPCAM), farletuzumab (FOLR1), glembatumumab (GPNMB), trastuzumab and pertuzumab (HER2), etaracizumab (integrin), anetumab (mesothelin), pankomab (MUC1), enfortumab (Nectin-4), and H8, A1, and A3 (5T4).

In a preferred embodiment of the invention, the antibody is selected from the group consisting of an anti-CD115 antibody, an anti-CD123, an anti-c-MET antibody, an anti-Cripto antibody, an anti-FAP antibody, an anti-GPNMB antibody, an anti-HER2 antibody, an anti-integrin antibody, an anti-Lewis Y antibody, an anti-MUC1 antibody, an anti-MUC16 antibody, an anti-PSMA antibody, an anti-5T4, an anti-TF antibody, an anti-TF-Ag antibody, an anti-Tag72 antibody and an anti-TROP2 antibody.

In another embodiment, the antibody to be used in the process of the present invention is a bispecific antibody (or a divalent fragment thereof) against a combination of two targets selected from the group listed above.

The antibody to be used in accordance with the present invention preferably is a monoclonal antibody (mAb) and can be a chimeric, humanized or human mAb. More preferably, in accordance with the present invention a humanized or human mAb is used, even more preferably a humanized or human IgG antibody, most preferably a humanized or human IgG$_1$ mAb. Preferably, said antibody has κ (kappa) light chains, i.e., a humanized or human IgG$_1$-κ antibody.

In humanized antibodies, the antigen-binding CDRs in the variable regions are derived from antibodies from a non-human species, commonly mouse, rat or rabbit. These non-human CDRs are placed within a human framework (FR1, FR2, FR3 and FR4) of the variable region, and are combined with human constant regions. Like human antibodies, these humanized antibodies can be numbered according to the Kabat and Eu numbering systems.

As one representative example, the antibody to be used in accordance with the present invention is the anti-PSMA antibody having an engineered cysteine at position 41 of the heavy chain (i.e. HC41C) that is disclosed in WO2015/177360 as SYD1030 (the heavy chain comprises the amino acid sequence of SEQ ID NO:2 and the light chain comprises the amino acid sequence of SEQ ID NO:5).

As another representative example, the antibody to be used in accordance with the present invention is the anti-5T4 antibody that is disclosed in WO2015/177360 as H8-HC41C (the heavy chain comprises the amino acid sequence of SEQ ID NO:8 and the light chain comprises the amino acid sequence of SEQ ID NO:11).

The process of the present invention is performed under mild conditions, i.e. conditions under which the antibody is stable. The reaction temperature typically is in the range of from 0° C. to 40° C., the pH typically is in the range of from 4 to 8. Preferred is a pH in the range of from 4 to 7. More preferred is a pH in the range of from 5 to 6.

Typically, the selective reduction reaction in accordance with the present invention is performed in a buffered aqueous solution. The cysteine-engineered antibodies that are produced in (mammalian) host cells and that are isolated and purified using conventional equipment and procedures may need a buffer exchange in order to obtain the optimal conditions for the selective reduction process in accordance with the present invention. Suitable buffers include a phosphate-buffered saline (PBS), a citrate, a histidine, an acetate or a succinate buffered aqueous solution. Additional salts and other solutes (e.g. sucrose, trehalose, EDTA) may be present in the buffered aqueous solution. A preferred buffer is a histidine buffer. The above-described reaction conditions mainly affect the rate and degree of completion of the selective reduction process and/or the stability of the antibody.

In one embodiment of the present invention, the process comprises reacting a cysteine-engineered antibody with a compound according to formula (I), (II), (III), (IV), (V), (VI) or (VII), wherein the compound is present in an amount of at least one molar equivalent per molar amount of engineered cysteine. This means that in order to selectively reduce an antibody having one engineered cysteine in the light or heavy chain, i.e. two engineered cysteines are present in the antibody, at least two moles of reducing agent are used per mole of antibody. Preferred is a process wherein an amount of from 2 to 16 molar equivalents per (molar amount of) engineered cysteine is used. If less than one molar equivalent per molar amount of engineered cysteine is used, complete reduction of all engineered cysteines is not achieved. The molar ratio of reducing agent per engineered cysteine affects the rate of reduction (uncapping) of the engineered cysteines, but it has no influence on the selectivity of the reduction. Unreacted, excess reducing agent is removed before converting the uncapped antibody into an antibody conjugate, typically by ultrafiltration/diafiltration (UF/DF), tangential flow filtration (TFF) or active carbon filtration. The possibility to remove the excess reducing agent by a fast active carbon filtration step is advantageous as UF/DF and TFF are quite laborious.

The present invention further relates to a process for the preparation of an antibody conjugate, comprising the process for the selective reduction of a cysteine-engineered antibody as described hereinabove. Typically, the process for the preparation of an antibody conjugate in accordance with the invention further comprises conjugation with a therapeutic moiety (e.g. a toxin or drug), a radiopharmaceutical (e.g. indium pendetide), a fluorescent label (e.g. fluorescein) or a hydrophilic polymer (e.g. polyethylene glycol, PEG) via a cleavable or non-cleavable linker. The methods for conjugation through reduced wild type or engineered cysteines known in the art are suitable to use in the process for the preparation of an antibody conjugate according to the invention.

As the process for the selective reduction according to the present invention does not break the interchain disulfide bonds formed by native cysteine residues, no wild-type conjugation occurs, no conjugates via mAb half body are formed (see FIG. 2), and the process results in a lower amount of high molecular weight (HMW) species, as compared to the conventional site specific conjugation procedure (see Table 2). Thus, the process of the present invention enables selective conjugation via uncapped engineered cysteines, without conjugation to uncapped wild-type cysteines, leading to a more homogeneous antibody conjugate product. The antibody conjugation process will be described herein below in more detail for antibody-drug conjugates (ADCs). Advantageously, the process according to the present invention is a two-step procedure: selective reduction of a cysteine-engineered antibody followed by antibody conjugation. The conventional conjugation procedure for ADCs, however, comprises three steps, i.e. (i) complete reduction of a cysteine-engineered antibody, (ii) partial re-oxidation of interchain disulfide bonds, and (iii) antibody conjugation. Examples of the conventional site-specific conjugation procedure are disclosed in Examples 11 and 12 of WO2006/034488, which describe site-specific conjugation of a maytansinoid (DM1)-comprising linker drug to an antibody, or the procedure disclosed by Doronina et al. Bioconjugate Chem., 2006, 17, 114-124, which describes antibody conjugation with mc-MMAF.

Preferably, the process for the preparation of an antibody conjugate according to the present invention further comprises conjugating a therapeutic moiety (e.g. a toxin or drug) via a cleavable or non-cleavable linker to form an antibody-drug conjugate or ADC.

The linker to be used in accordance with the present invention should comprise a functional group which can react with the thiol group of an uncapped engineered cysteine, e.g. a maleimide or a haloacetyl group. Preferably, the linker used is a cleavable linker. Suitable cleavable linkers are known in the art and comprise e.g. a valine-citrulline (vc) or a valine-alanine (va) moiety.

The antibody conjugation process in accordance with the present invention may be performed in a buffered aqueous solution, e.g. a phosphate-buffered saline (PBS), a citrate, a histidine or a succinate buffered aqueous solution, at a pH and temperature at which the antibody, the moiety to be conjugated (e.g. a linker toxin, linker drug or linker fluorescent label), and the resulting antibody conjugate are stable. Typically, the pH is in the range of from 5 to 8, and the temperature is in the range of from 0° C. to 40° C. Additional salts and other solutes (e.g. sucrose, trehalose, EDTA) may be present in the buffered aqueous solution. In case the therapeutic moiety to be conjugated to the antibody is poorly water soluble, e.g. in case of a hydrophobic linker drug, the therapeutic moiety may be dissolved in an organic, water-miscible solvent. Suitable solvents include dimethyl sulfoxide (DMSO), dimethyl acetamide (DMA), propylene glycol, and ethylene glycol.

The resulting antibody conjugates may be purified using standard methods known to the person skilled in the art, e.g. active carbon filtration to remove excess linker drug and hydrophobic interaction chromatography (HIC) to remove any unreacted antibody.

The antibody conjugates prepared according to the process of the present invention may be analyzed using analytical methods known in the art, e.g. HPLC, shielded hydrophobic phase HPLC (SHPC), HIC, and size-exclusion chromatography (SEC).

Preferred in accordance with the present invention is a process for the preparation of an ADC wherein the therapeutic moiety is a toxin or drug.

More preferred is a process for the preparation of an ADC wherein the therapeutic moiety is a tubulin inhibitor (e.g. a maytansinoid, auristatin or tubulysin derivative), a ribosome-inactivating protein (e.g. a saporin derivative), a DNA minor groove binding agent (e.g. a duocarmycin or pyrrolobenzodiazepine (PBD) derivative), a DNA damaging agent (e.g. a PBD derivative), a DNA alkylating agent (e.g. a duocarmycin derivative), a DNA intercalating agent (e.g. a calicheamicin derivative), a DNA crosslinking agent (e.g. a a 1-(chloromethyl)-2,3-dihydro-1H-benzo[e]indole (CBI) dimer derivative), an RNA polymerase inhibitor (e.g. an amanitin derivative), a DNA cleaving agent (e.g. a calicheamicin derivative) or an agent that disrupts protein synthesis or the function of essential cellular proteins (e.g. a topoisomerase I or II inhibitor (e.g. a camptothecin derivative), a proteasome inhibitor, a histone deacetylase inhibitor, a nuclear export inhibitor, a kinase inhibitor, or an inhibitor of heat shock protein 90).

Even more preferred is a process for the preparation of an ADC wherein the therapeutic moiety is a duocarmycin, a CBI dimer, a calicheamicin, a PBD, a PBD dimer, a maytansinoid, a tubulysin, a camptothecin, an amanitin, or an auristatin derivative. Most preferably, the therapeutic moiety is a duocarmycin derivative.

Examples of suitable therapeutic moieties include the duocarmycin seco-DUBA, the calicheamicin N-acetyl gamma calicheamicin dimethyl hydrazide (CalichDMH), the PBD dimer SGD-1882, the maytansinoids DM1 and DM4, and the auristatins monomethyl auristatin E (MMAE) and monomethyl auristatin F (MMAF).

Examples of suitable linker drugs (LD) include vc-seco-DUBA (SYD980), mertansine, emtansine, ravtansine, mc-vc-PAB-MMAE (also abbreviated as mc-vc-MMAE or vc-MMAE), mc-MMAF, and mc-vc-MMAF. These abbreviations are well-known to the skilled artisan (see also WO2015/177360). The linker drug vc-seco-DUBA is disclosed in WO2011/133039 as compound 18b on p. 210, ll. 21-27.

In one particular embodiment, the present invention relates to a process for the preparation of an ADC according to formula (VIII), wherein
n is 0-3, preferably 0-1,
m represents an average DAR of from 1 to 6, preferably of from 1 to 4,
$R^1$ is selected from

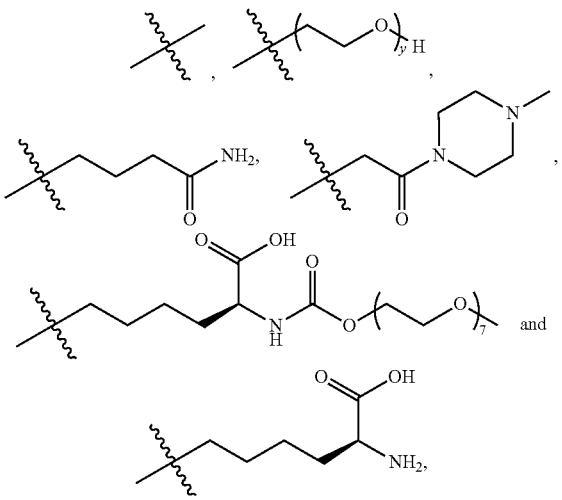

y is 1-16, and
$R^2$ is selected from

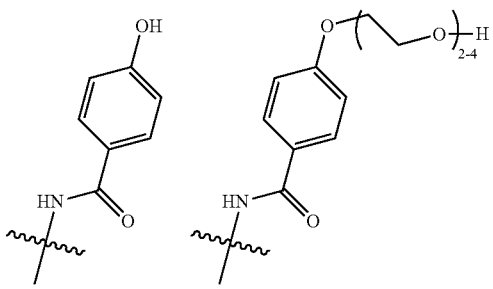

(VIII)

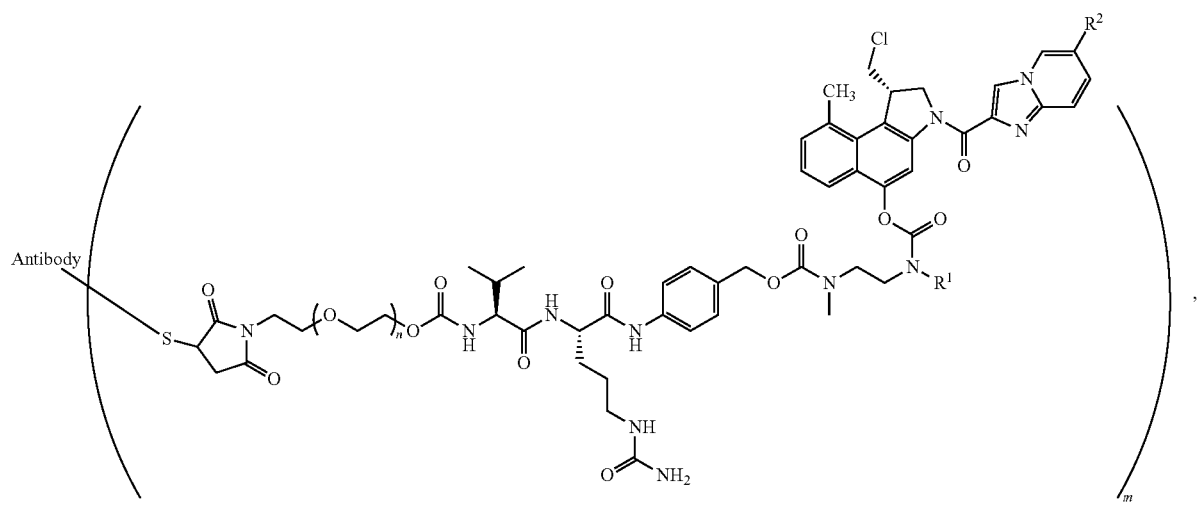

,

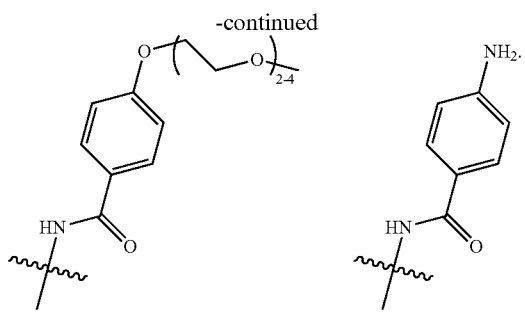

Preferred is a process according to the present invention for the preparation of an ADC according to formula (IX)

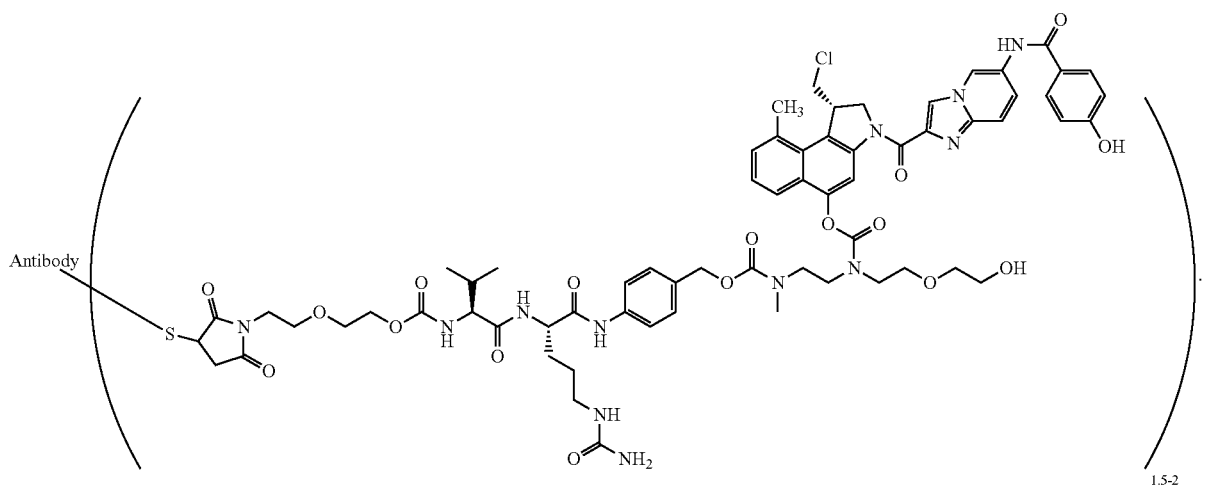

(IX)

EXAMPLES

Materials and Methods

Cysteine-engineered antibodies were obtained using the materials and procedures described in WO2015/177360. Reagents and buffers were procured from commercial suppliers. Compounds according to formula (I), i.e. 2-(diphenylphosphino)benzenesulfonic acid, and (II), i.e. 2-(dicyclohexylphosphino)benzenesulfonic acid, 3-(diphenylphosphino)benzenesulfonic acid, 4-(diphenylphosphino)benzenesulfonic acid, and triphenylphosphine-3,3',3''-trisulfonic acid were purchased from Sigma-Aldrich. The compounds according to formula (III), (IV), (V), (VI) and (VII) were prepared by lithiating benzenesulfonic acid, followed by reacting the lithiated benzenesulfonic acid with the appropriate dialkyl, diaryl or alkyl/aryl (chloro)phosphine using procedures analogous to literature procedures, e.g. M. Bornand et al., Organometallics, 2007, 26(14), 3585-3596 and T. Schultz et al., Synthesis, 2005, 6, 1005-1011. Reduction of the engineered cysteines and conjugation of linker drug (vc-seco-DUBA) was performed according to either protocol A or protocol B as described hereinbelow. The linker drug vc-seco-DUBA was synthesized according to procedures as described in WO2011/133039. The resulting ADCs were analyzed using SDS-PAGE, HIC, SHPC, and SEC. The results are described in Tables 1 and 2 (and in FIGS. 1 and 2).

SDS-PAGE—For non-reducing SDS-PAGE gel electrophoresis, a sample was diluted to 0.2 mg/mL using purified water (Milli-Q), followed by a 1 to 1 dilution with electrophoresis buffer (65.8 mM TRIS.HCl, pH 6.8, 26.3% (w/v) glycerol, 2.1% SDS, 0.01% bromophenol blue, 2× Laemmli sample buffer (Bio-Rad, Cat. no. 161-0737)). The mixture was incubated at 70° C. for 10 minutes. 1 µg (10 µL) was loaded per slot onto a precast gel 4-20% (Criterion TGX Stain free Bio-Rad, Cat. no. 567-8094), additionally one or more slots were loaded with an unstained standard marker (Precision Plus Protein™ Unstained Protein Standards, Strep-tagged recombinant, Bio-Rad Cat. no. 161-0363). Gel electrophoresis was performed at 300 V for ±20-25 minutes in TRIS/glycine/SDS buffer (25 mM TRIS, 1.92 M glycine, 0.1% SDS, pH 8.3, Bio-Rad Cat. no. 161-0772). The gels were imaged in a gel imaging system (Gel Doc® Ez System Bio-Rad Cat. no. 1708270).

HIC—For analytical HIC, 5-10 µL of sample (1 mg/ml) was injected onto a TSKgel Butyl-NPR column (4.6 mm ID×3.5 cm L, Tosoh Bioscience, Cat. no. 14947). The elution method consisted of a linear gradient from 100% Buffer A (25 mM sodium phosphate, 1.5 M ammonium sulphate, pH 6.95) to 100% of Buffer B (25 mM sodium phosphate, pH 6.95, 20% isopropanol) at 0.4 ml/min over 20 minutes. The column temperature was maintained at 25° C. A Waters Acquity H-Class UPLC system equipped with PDA-detector and Empower software was used. Absorbance was measured at 214 nm to quantify the average DAR.

SHPC—Samples were prepared by mixing 70 µl ADC solution with 30 µl DMA. 50 µl of the samples was injected onto a shielded hydrophobic phase column (SUPELCOSIL LC-HISEP 5 µm, 4.6 mm ID×15 cm L, Supelco (Sigma-Aldrich), Cat. no. 58935) mounted in an ultra performance liquid chromatography (UPLC) system (Waters Acquity H-Class UPLC system equipped with PDA-detector and Empower software). The elution method consisted of a linear gradient from 90% Buffer A (100 mM ammonium acetate, pH 4.0) and 10% of Buffer B (acetonitrile) to 32% Buffer A and 68% Buffer B at 1.0 ml/min over 10 minutes. The column temperature was maintained at 45° C. Absorbance was measured at 325 nm to quantify the amount of free linker drug (LD).

SEC—For analytical SEC, 5 μL of sample (1 mg/ml) was injected onto a TSKgel G3000SWXL column (5 μm, 7.8 mm ID×30 cm L, Tosoh Bioscience, Cat. no. 08541) equipped with a TSKgel SWXL Guard column (7 μm, 6.0 mm ID×4.0 cm L, Tosoh Bioscience, Cat. no. 08543). The elution method consisted of elution with 100% 50 mM sodium phosphate, 300 mM NaCl, pH 7.5 at 0.6 ml/min for 30 minutes. The column temperature was maintained at 25° C. A Waters Acquity H-Class UPLC system equipped with PDA-detector and Empower software was used. Absorbance was measured at 214 nm to quantify the amount of HMW species.

A. General Protocol Selective Reduction/Site-Specific Conjugation According to the Invention

Reduction

A solution of cysteine-engineered antibody (10-40 mg/ml in 15 mM histidine, 50 mM sucrose, 0.01% polysorbate-20, pH 5) was diluted with 100 mM histidine, pH 5 (±1300 μl), and EDTA (25 mM in water, 5% v/v). 2-(Diphenylphosphino)benzenesulfonic acid (DPPBS, compound (I)) (10 mM in water, 2-32 equivalents) was added and the resulting mixture was incubated at room temperature (RT) for 16-24 hrs. The excess DPPBS was removed by a centrifugal concentrator (Vivaspin filter, 30 kDa cut-off, PES) using 4.2 mM histidine, 50 mM trehalose, pH 6.

Similar conditions were used for the reduction using compounds (II)-(VII).

Conjugation

The pH of the resulting antibody solution was kept at 6 or raised to ~7.4 using TRIS (1 M in water, pH 8) after which DMA was added followed by a solution of linker drug (10 mM in DMA). The final concentration of DMA was 5-10%. The resulting mixture was incubated overnight at RT in the absence of light in case of pH 6 or for 2-3 hrs in case of pH 7.4. In order to remove the excess of linker drug, activated charcoal was added and the mixture was incubated at RT for at least 0.5 hr. The charcoal was removed using a 0.2 μm PES filter and the resulting ADC was formulated in 4.2 mM histidine, 50 mM trehalose, pH 6 using a Vivaspin centrifugal concentrator (30 kDa cut-off, PES).

B. General Protocol Conventional Site-Specific Conjugation

Reduction

A solution of cysteine-engineered antibody (250 μl, 48 mg/ml in 15 mM histidine, 50 mM sucrose, 0.01% polysorbate-20, pH 6) was diluted with 4.2 mM histidine, 50 mM trehalose, pH6 (750 μl), and EDTA (25 mM in water, 4% v/v). The pH was adjusted to ~7.4 using TRIS.HCl (1 M in water, pH 8) after which TCEP (10 mM in water, 20 equivalents) was added and the resulting mixture was incubated at RT for 1-3 hrs. The excess TCEP was removed by a Vivaspin centrifugal concentrator (30 kDa cut-off, PES) using 4.2 mM histidine, 50 mM trehalose, pH 6.

Conjugation

The pH of the resulting antibody solution was raised to ~7.4 using TRIS.HCl (1 M in water, pH 8) after which dehydroascorbic acid (10 mM in water, 20 equivalents) was added and the resulting mixture was incubated at RT for 2 hrs. DMA was added followed by a solution of linker drug (10 mM in DMA). The final concentration of DMA was 5-10%. The resulting mixture was incubated at RT in the absence of light for 1-2 hrs. In order to remove the excess of linker drug, activated charcoal was added and the mixture was incubated at RT for at least 0.5 hr. The charcoal was removed using a 0.2 μm PES filter and the resulting ADC was formulated in 4.2 mM histidine, 50 mM trehalose, pH 6 using a Vivaspin centrifugal concentrator (30 kDa cut-off, PES).

Results

FIG. 1 shows an SDS-PAGE gel run under non-reducing conditions (as described above) of reaction mixtures of a heavy chain 41 engineered cysteine (HC41C) anti-PSMA antibody incubated with four different reducing agents in lanes 1, 2, 3 and 4 for 8 days at ambient temperature. The numbering of the structures corresponds with the lanes. Structure 2 is a compound according to Formula (I). The band corresponding to the molecular weight (MW) of an intact antibody is labeled LHHL, the bands corresponding to the MW of the heavy chain are labeled H, those corresponding to the MW of the light chain are labeled L. Incubation with compounds 1, 3 and 4 results in reduction of the interchain disulfides, indicated by the absence of intact antibody and the presence of heavy chain and light chain bands. However, compound 2 does not reduce the interchain disulfides, as indicated by the absence of heavy chain and light chain bands and the presence of intact antibody.

Figure 2:
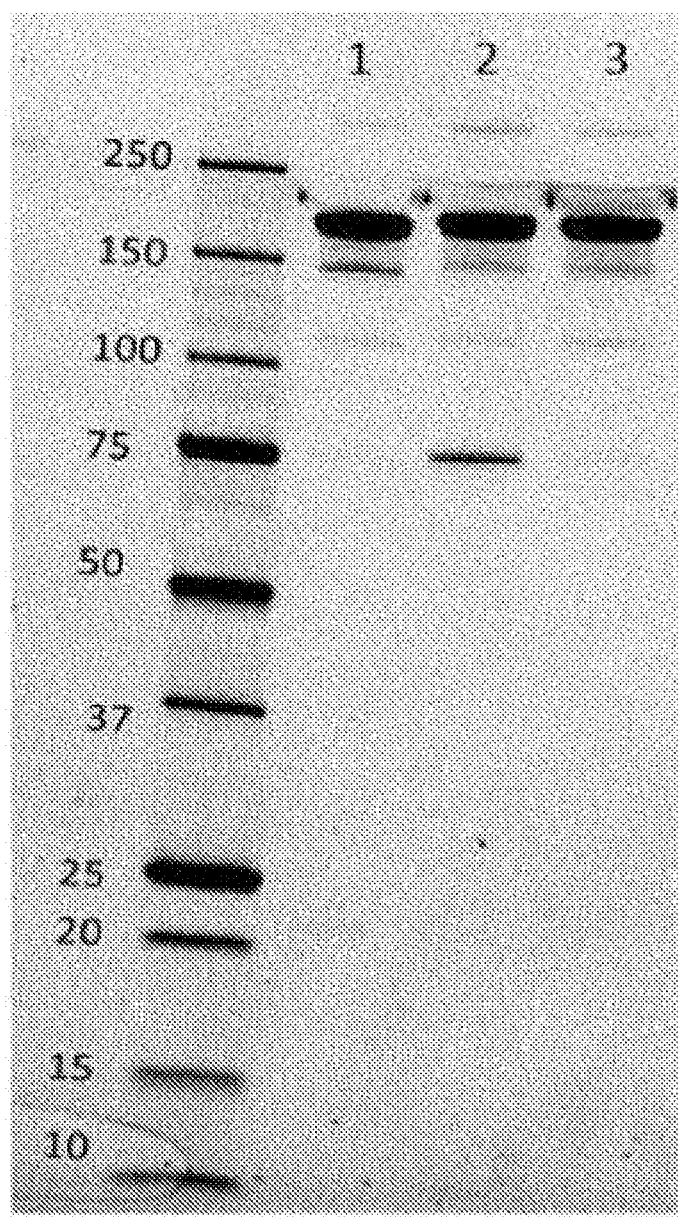
FIG. 2 shows an SDS-PAGE gel run under non-reducing conditions of reaction mixtures of a HC41C anti-PSMA vc-seco-DUBA ADC following conventional site-specific conjugation using protocol B in lane 2 and following conjugation after selective reduction using protocol A in lane 3, with the un-conjugated HC41C anti-PSMA antibody in lane 1.

FIG. 2 shows an SDS-PAGE gel run under non-reducing conditions of reaction mixtures of a HC41C anti-PSMA vc-seco-DUBA ADC following conventional site-specific conjugation using protocol B in lane 2 and following conjugation after selective reduction using protocol A in lane 3 (using DPPBS, compound (I)), with the unconjugated HC41C anti-PSMA antibody in lane 1, serving as control for the absence of mAb half body. The band corresponding to the MW of 75 kDa indicates the presence of mAb half body and is present in lane 2. Thus, protocol B results in the formation of mAb half body. However, the absence of this band in lane 3 indicates that no half body is formed during the selective reduction/conjugation process according to protocol A.

Using the procedures described above, the ADC products obtained using protocols A and B were analyzed. The results are summarized in Table 1 and 2.

TABLE 1

Results of reduction/conjugation of various cysteine-engineered antibodies using compound (I)[1]

| vc-seco-DUBA ADC | Cys mutation | | Compound (I) |
|---|---|---|---|
| | HC | LC | |
| Anti-PSMA | 41C | wt | ++ |
| Anti-PSMA | 152C | wt | ++ |
| Anti-PSMA | 153C | wt | ++ |
| Anti-PSMA | wt | 40C | ++ |
| Anti-PSMA | wt | 41C | ++ |
| Anti-PSMA | wt | 165C | ++ |

TABLE 1-continued

Results of reduction/conjugation of various cysteine-engineered antibodies using compound (I)[1]

| vc-seco-DUBA ADC | Cys mutation HC | Cys mutation LC | Compound (I) |
|---|---|---|---|
| H8 | 40C | wt | +/− |
| H8 | 41C | wt | ++ |
| Trastuzumab | 41C | wt | ++ |

++ selective and fast reaction,
+/− selective but slow reaction,
wt wild type
[1]Compounds (I), (II), (V), (VI) and (VII) were tested using the anti-PSMA HC41C antibody and exhibited slow selective reduction.

Compounds (I), (II), (V), (VI) and (VII) did not reduce the interchain disulfides; the compounds only reduced the engineered cysteine. Compound (I) reduces the engineered cysteine at a higher rate than compounds (II), (V), (VI) and (VII). H8-HC40C is reduced with a slow rate.

TABLE 2

Comparison between reduction/conjugation protocols A and B
Protocol A is the general protocol for selective reduction/site-specific conjugation according to the invention, while protocol B is the general protocol for the conventional reduction/site-specific conjugation
Anti-PSMA vc-seco-DUBA HC41C ADC

| | Protocol | A | B |
|---|---|---|---|
| % monomer | SEC | 99.0 | 97.9 |
| % HMW | SEC | 1.0 | 2.1 |
| % mAb half body | SDS-PAGE | 0 | 6 |
| avg DAR | HIC | 1.80 | 1.80 |
| % DAR0 | HIC | 1.6 | 1.5 |
| % free LD | SHPC | <LOD | <LOD |

DAR0 = naked antibody

The ADC product obtained with protocol A contains a higher amount of monomer and a lower amount of high molecular weight agregates and mAb half body than the ADC product obtained with protocol B. Thus protocol A results in a more homogenous ADC product than protocol B.

The invention claimed is:

1. A process, which comprises reacting an antibody comprising one or more engineered cysteines at positions selected from heavy chain 40, 41, 42 and 89 according to the Kabat numbering system, heavy chain 152, 153, 155, and 171 according to the Eu numbering system, light chain 40 and 41 according to the Kabat numbering system, and light chain 165 and 168 according to the Eu numbering system, with a compound according to formula (I), (II), (III), (IV), (V), (VI) or (VII)

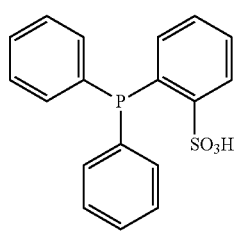
(I)

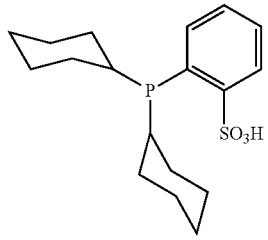
(II)

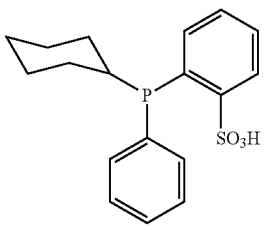
(III)

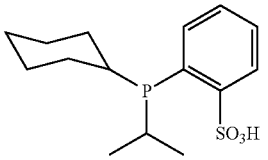
(IV)

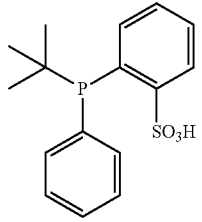
(V)

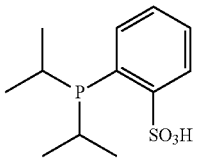
(VI)

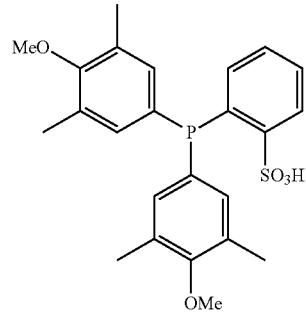
(VII)

or a salt thereof, to reduce said one or more engineered cysteines.

2. The process according to claim 1, wherein the antibody comprises one or more engineered cysteines at positions selected from heavy chain 40, 41, 42, 152, and 153 and light chain 40, 41, and 165.

3. The process according to claim 1, wherein the antibody comprises one or more engineered cysteines at positions selected from heavy chain 41 and 42, and light chain 40 and 41.

4. The process according to claim 1, wherein the compound according to formula (I), (II), (III), (IV), (V), (VI) or (VII) is present in an amount of at least one molar equivalent per molar amount of engineered cysteine.

5. The process according to claim 1, wherein the antibody is a monospecific antibody against one of the targets selected from the group consisting of annexin A1, B7H4, CA6, CA9, CA15-3, CA19-9, CA125, CA242, CCR2, CCR5, CD2, CD19, CD20, CD22, CD30, CD33, CD37, CD38, CD40, CD44, CD47, CD56, CD70, CD74, CD79, CD115, CD123, CD138, CD203c, CD303, CD333, CEA, CEACAM, CLCA-1, CLL-1, c-MET, Cripto, CTLA4, DLL3, EGFL, EGFR, EPCAM, EPh antibodies, such as EphA2 or EPhB3, ETBR, FAP, FcRL5, FGF, FGFR3, FOLR1, GCC, GPNMB, HER2, HMW-MAA, integrin, IGF1R, L6, Lewis A like carbohydrate, Lewis X, Lewis Y, LIV1, mesothelin, MUC1, MUC16, NaPi2b, Nectin-4, PSMA, PTK7, SLC44A4, STEAP-1, 5T4 (or TPBG, trophoblast glycoprotein), TF (tissue factor), TF-Ag, Tag72, TNF, TROP2, VEGF and VLA; or a bispecific antibody against a combination of two targets selected from said group.

6. The process according to claim 1, further comprising conjugating said reduced engineered cysteine with a therapeutic moiety, a radiopharmaceutical, a fluorescent label or a hydrophilic polymer via a cleavable or non-cleavable linker to form an antibody conjugate.

7. The process according to claim 6, wherein the therapeutic moiety is a tubulin inhibitor, a ribosome-inactivating protein, a DNA minor groove binding agent, a DNA damaging agent, a DNA alkylating agent, a DNA intercalating agent, a DNA crosslinking agent, an RNA polymerase inhibitor, a DNA cleaving agent or an agent that disrupts protein synthesis or the function of essential cellular proteins.

8. The process according to claim 6, wherein the therapeutic moiety is a duocarmycin, a CBI dimer, a calicheamicin, a PBD, a PBD dimer, a maytansinoid, a tubulysin, a camptothecin, an amanitin or an auristatin derivative.

9. The process according to claim 6, wherein said antibody conjugate is according to formula (VIII), wherein
n is 0-3,
m represents an average DAR of from 1 to 6,
$R^1$ is selected from

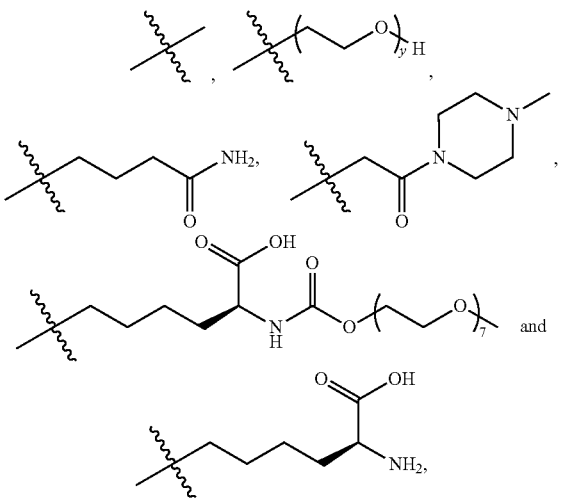

y is 1-16, and
$R^2$ is selected from

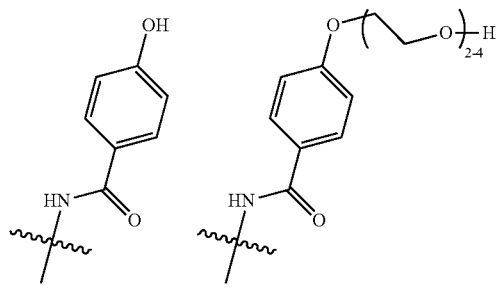

(VIII)

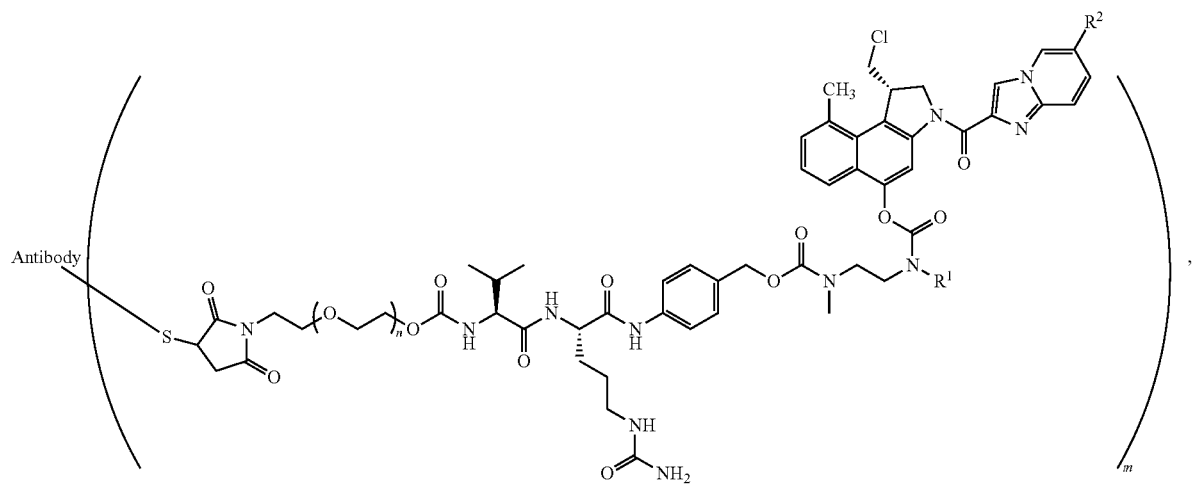

-continued

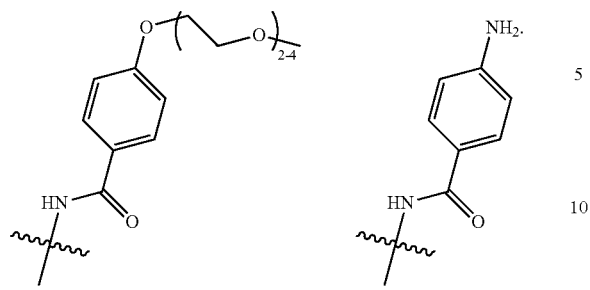

10. The process according to claim 9, wherein said antibody conjugate is according to formula (IX)

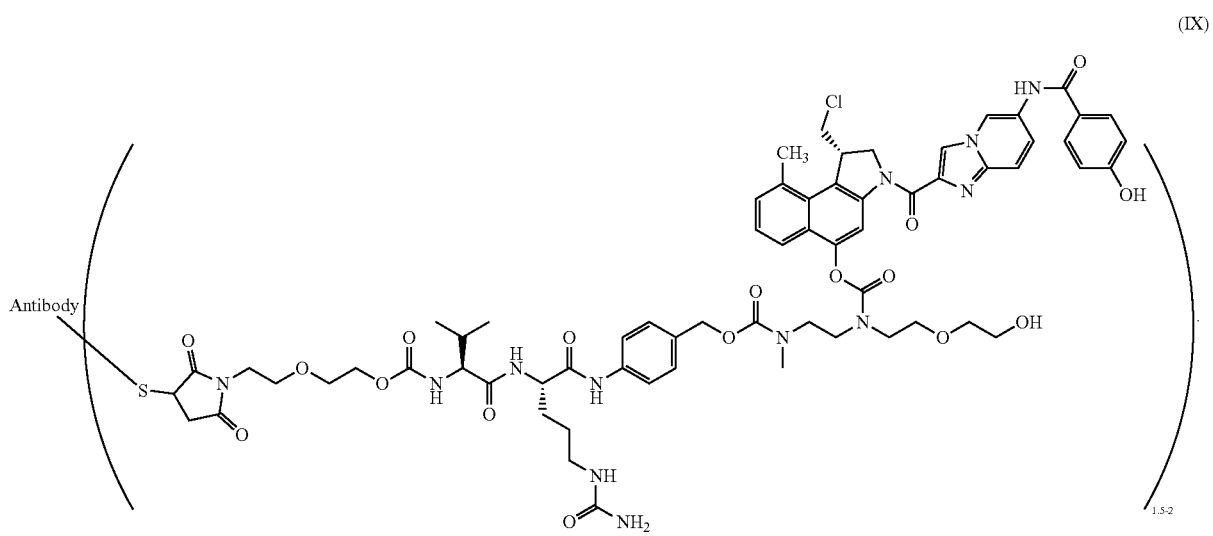

(IX)

11. The process according to claim 1, wherein said reaction is carried out in a buffered aqueous solution.

12. The process according to claim 6, wherein the compound according to formula (I), (II), (III), (IV), (V), (VI) or (VII) is present in an amount of 2 to 16 molar equivalents per engineered cysteine of said antibody.

13. The process according to claim 12, which further comprises removing any unreacted reducing agent prior to said conjugation reaction.

14. The process according to claim 13, wherein said removing step does not use ultrafiltration/diafiltration (UF/DF) or tangential flow filtration (TFF).

15. The process according to claim 13, wherein said removing step uses active carbon filtration.

16. The process according to claim 6, wherein said reduction reaction is carried out in a buffered aqueous solution.

17. The process according to claim 3, wherein the antibody comprises one engineered cysteine at heavy chain position 41.

18. The process according to claim 1, wherein the compound is a compound according to formula (I) or a salt thereof.

19. The process according to claim 1, wherein the antibody is selected from the group consisting of an anti-CD115 antibody, an anti-CD123 antibody, an anti-c-MET antibody, an anti-Cripto antibody, an anti-FAP antibody, an anti-GPNMB antibody, an anti-HER2 antibody, an anti-integrin antibody, an anti-Lewis Y antibody, an anti-MUC1 antibody, an anti-MUC16 antibody, an anti-PSMA antibody, an anti-5T4 antibody, an anti-TF antibody, an anti-TF-Ag antibody, an anti-Tag72 antibody and an anti-TROP2 antibody.

20. The process according to claim 8, wherein the therapeutic moiety is a duocarmycin derivative.

* * * * *